(12) United States Patent
McArdle et al.

(10) Patent No.: US 8,053,589 B1
(45) Date of Patent: Nov. 8, 2011

(54) IMINES AND METHODS OF PREPARING ELECTRON DEFICIENT OLEFINS USING SUCH NOVEL IMINES

(75) Inventors: Ciaran B. McArdle, Dublin (IE); Ligang Zhao, Goettingen (DE)

(73) Assignee: Henkel Ireland Limited, Whitestown (IE)

( * ) Notice: Subject to any disclaimer, the term of this patent is extended or adjusted under 35 U.S.C. 154(b) by 746 days.

(21) Appl. No.: 11/877,703

(22) Filed: Oct. 24, 2007

(51) Int. Cl.
C07C 255/00 (2006.01)

(52) U.S. Cl. ........................................ 558/372; 558/374

(58) Field of Classification Search ........................ None
See application file for complete search history.

(56) References Cited

U.S. PATENT DOCUMENTS

| | | | |
|---|---|---|---|
| 2,363,464 A | 11/1944 | Senkus | |
| 2,413,249 A | 12/1946 | Senkus | |
| 2,413,250 A | 12/1946 | Senkus | |
| 2,415,046 A | 1/1947 | Senkus | |
| 2,582,128 A * | 1/1952 | Hurwitz | 564/271 |
| 2,721,858 A | 10/1955 | Joyner et al. | |
| 2,756,251 A | 7/1956 | Joyner et al. | |
| 2,763,677 A | 9/1956 | Jeremias | |
| 2,870,193 A | 1/1959 | Pollack et al. | |
| 3,142,698 A | 7/1964 | Halpern et al. | |
| 3,282,773 A | 11/1966 | Wicker | |
| 3,554,987 A | 1/1971 | Smith | |
| 3,903,055 A | 9/1975 | Buck | |
| 3,975,422 A | 8/1976 | Buck | |
| 3,988,299 A | 10/1976 | Malofsky | |
| 3,995,641 A | 12/1976 | Kronenthal et al. | |
| 4,003,942 A | 1/1977 | Buck | |
| 4,012,402 A | 3/1977 | Buck | |
| 4,013,703 A | 3/1977 | Buck | |
| 4,056,543 A | 11/1977 | Ponticello | |
| 4,160,864 A | 7/1979 | Ponticello | |
| 4,202,920 A | 5/1980 | Renner et al. | |
| 4,364,876 A | 12/1982 | Kimura et al. | |
| 4,440,910 A | 4/1984 | O'Connor | |
| 4,512,357 A | 4/1985 | Earl | |
| 4,556,700 A | 12/1985 | Harris et al. | |
| 4,560,723 A | 12/1985 | Millet | |
| 4,587,059 A | 5/1986 | Harth et al. | |
| 4,622,414 A | 11/1986 | McKervey | |
| 4,636,539 A | 1/1987 | Harris et al. | |
| 4,695,615 A | 9/1987 | Leonard et al. | |
| 4,718,966 A | 1/1988 | Harris et al. | |
| 4,764,545 A * | 8/1988 | Yosida | 523/212 |
| 4,837,260 A | 6/1989 | Sato et al. | |
| 4,855,461 A | 8/1989 | Harris | |
| 4,876,045 A * | 10/1989 | Longo et al. | 552/526 |
| 4,906,317 A | 3/1990 | Liu | |
| 5,142,098 A | 8/1992 | Bru-Magniez et al. | |
| 5,288,794 A | 2/1994 | Attarwala | |
| 5,306,752 A | 4/1994 | Attarwala | |
| 5,312,864 A | 5/1994 | Wenz et al. | |
| 5,328,944 A | 7/1994 | Attarwala et al. | |
| 5,340,873 A | 8/1994 | Mitry | |
| 5,386,047 A | 1/1995 | Nakos et al. | |
| 5,424,343 A | 6/1995 | Attarwala | |
| 5,424,344 A | 6/1995 | Lewin | |
| 5,455,369 A | 10/1995 | Meier et al. | |
| 5,624,699 A | 4/1997 | Lang | |
| 5,703,267 A | 12/1997 | Takahashi et al. | |
| 5,744,642 A | 4/1998 | Lantzsch et al. | |
| 5,994,464 A | 11/1999 | Ohsawa | |
| 6,093,780 A | 7/2000 | Attarwala | |
| 6,096,848 A | 8/2000 | Gololobov et al. | |
| 6,174,919 B1 | 1/2001 | Hickey | |
| 6,245,933 B1 | 6/2001 | Malofsky et al. | |
| 6,291,544 B1 | 9/2001 | Kotzev | |
| 6,531,460 B1 * | 3/2003 | Takenouchi et al. | 514/167 |
| 6,833,196 B1 | 12/2004 | Wojciak | |
| 6,835,789 B1 | 12/2004 | Kneafsey et al. | |
| 2006/0094833 A1 | 5/2006 | McDonnell et al. | |
| 2006/0269870 A1 | 11/2006 | Harada et al. | |
| 2008/0241249 A1 | 10/2008 | Quintero et al. | |

FOREIGN PATENT DOCUMENTS

| | | |
|---|---|---|
| DE | 2 626 173 | 12/1977 |
| DE | 40 34 080 A1 | 6/1991 |
| DE | 19519958 | 12/1995 |
| EP | 0 127 855 | 12/1984 |
| EP | 0 267 981 A | 5/1988 |
| EP | 0 459 617 A1 | 12/1991 |
| WO | WO 94/15590 A1 | 7/1994 |
| WO | WO 94/15907 | 7/1994 |
| WO | WO 95/32183 | 11/1995 |
| WO | WO 99/14206 A1 | 3/1999 |
| WO | WO 03/006225 A1 | 1/2003 |
| WO | WO 03/086605 A2 | 10/2003 |

OTHER PUBLICATIONS

Carl J. Buck, Unequivocal Synthesis of Bis(2-Cyanoacrylate) Monomers, I. Via Anthracene Adducts, *Journal of Polymer Science, Polymer Chemistry Edition*, vol. 16, 2475-507 (1978).

G. Jones, "The Knoevenagle Condensation", *Organic Reactions*, vol. XV, 204, Wiley New York (1967).

F. Bigi et al., "Montmorillonite KSF as an Inorganic, Water Stable, and Reusable Catalyst for the Knoevenagel Synthesis of Coumarin-3-carboxylic Acids", *Journal Organic Chemistry*, vol. 64, 1033-35 (1999).

B. Green et al., Synthesis of Steroidal 16, 17-Fused Unsaturated δ-Lactones[1,] *Journal Organic Chemistry*, vol. 50, 640-44 (1985).

P. Rao et al., "Zinc Chloride as a New Catalyst for Knoevenagel Condensation", *Tetrahedron Letters*, vol. 32, No. 41, 5821-22 (1991).

J. S. Yadav et al., "Phosphane-Catalyzed Knoevenagel Condensation: A Facile Synthesis of Cyanoacrylates and α-Cyanonitrites", *European Journal Organic Chemistry*, 546-51 (2004).

L. Tietze et al., Comprehensive Organic Synthesis, Pergamon Press, Oxford, vol. 2, Chapter 1.11, 341 (1991).

P. Laszlo, "Catalysis of Organic Reactions by Inorganic Solids", *Accounts of Chemical Research*, vol. 19, 121-27 (1986).

(Continued)

*Primary Examiner* — Paul A Zucker

(74) *Attorney, Agent, or Firm* — Steven C. Berman

(57) ABSTRACT

This invention relates to novel imines, some of which are in the form of ionic liquids, and a process for producing electron deficient olefins, such as 2-cyanoacrylates, using an imine, for instance such novel imines, many of which are in the form of an ionic liquid.

13 Claims, 4 Drawing Sheets

OTHER PUBLICATIONS

K. Kloestra et al., "Base and Acid Catalysis by the Alkali-containing MCM-41 Mesoporous Molecul Sieve", *Journal Chemical Soc. Chem. Commun.*, 1005-06 (1995).

P. Lednor et al., "The Use of a High Surface Area Silicon Oxynitride as a Solid, Basic Catalyst", *Journal Chemical Society, Chem. Commun.*, 1625-26 (1991).

F. Bigi et al., "A Revision of the Biginelli Reaction Under Solid Acid Catalysis. Solvent-free Synthesis of Dihydropyrimidines Over Montmorillonite KSF", *Tetrahedron Letters*, vol. 40, 3465-68 (1999).

F. Bigi et al., "Clean synthesis in water: uncatalysed preparation of ylidenemalononitriles", *Green Chemistry*, vol. 2, 101-03 (2000).

R. Breslow, "Hydrophobic Effects on Simple Organic Reactions in Water", *Accounts of Chemical Research*, vol. 24, 159-64 (1991).

C. Li, "Organic Reactions in Aqueous Media—With a Focus on Carbon-Carbon Bond Formation", *Chemical Reviews*, vol. 93, 2023-35 (1993).

T. Welton, "Room Temperature Ionic Liquids. Solvents for Synthesis and Catalysis", *Chemical Reviews*, vol. 99, 2071-83 (1999).

D. Morrison et al., "Base-promoted reactions in ionic liquid solvents. The Knoevenagel and Robinson annulation reactions", *Tetrahedron Letters*, vol. 42, 6053-55 (2001).

Fraga-Dubreiul et al., "Grafted ionic liquid-phase-supported synthesis of small organic molecules", *Tetrahedron Letter*, vol. 42, 6097-6100 (2001).

M. Smietana et al., "Preparation of Silyl Enol Ethers Using (Bistrimethylsilyl)acetamide in Ionic Liquids", *Organic Letters*, vol. 3, No. 7, 1037-39 (2001).

Li et al., "n-Butyl Pyridinium Nitrate as a Reusable Ionic Liquid Medium for Knoevenagel Condensation", *Chinese Chemical Letters*, vol. 14, No. 5, 448-50 (2003).

J. Harjani et al., "Lewis acidic ionic liquids for the synthesis of electrophilic alkenes via the Knoevenagel condensation", *Tetrahedron Letters*, vol. 43, 1127-30 (2002).

Xu et al., "Knoevenagel condensation Reaction Catalyzed by Functionalized Ionic Liquid 1-(2-Hydroxyethyl)-3-methyl Imidazolium Chloride", *Chinese Journal of Organic Chemistry*, vol. 24(10), 1253-56 (2004).

Su et al., "Organic Reactions in Ionic Liquids: Knoevenagel Condensation Catalyzed by Ethylenediammonium Diacetate", *Synthesis 2003*, No. 4, 555-59 (2003).

Moehrle et al., "Aminomethylierung von 1,3-Diketonen", *Pharmazie*, vol. 40, 697-701 (1985).

J. March, "Reactions", *Advanced Organic Chemistry*, 3$^{rd}$ Edition, Wiley & Sons Inc., 417 (1985).

J. March, "Addition to Carbon-Hetero Multiple Bonds", *Advanced Organic Chemistry*, 3$^{rd}$ Edition, Wiley & Sons, 802-03 (1985).

M. B. Smith, *Organic Synthesis*, McGraw Hill International Chemistry Series, 1302 (1994).

Tehrani et al., "Product Class 8: Iminium Salts", *Science of Synthesis*, vol. 27, 313-48 (2004).

B. Min et al., "Facile Synthesis of α-Substituted Acrylate Esters", *Journal of Organic Chemistry*, vol. 67, 7365-68 (2002).

Holy et al., "The Mannich Reaction-II Derivatization of Aldehydes and Ketones Using Dimethyl(methylene)ammonium Salts", *Tetrahedron Letters*, vol. 35, 613-19 (1979).

Bryson et al., "Preformed Mannich Salts: A Facile Preparation of Dimethyl(methylene)ammonium Iodide", *Journal of Organic Chemistry*, vol. 45, 524-25 (1980).

J. March, "The Pinacol Rearrangement", *Advanced Organic Chemistry*, 3$^{rd}$ Edition, Wiley & Sons, 963-64 (1985).

J. March, "Free-Radical Substitution", *Advanced Organic Chemistry*, 3$^{rd}$ Edition, Wiley & Sons, 642 (1985).

Jahn et al., "A Novel and Simple Method for the Preparation of Iminium Salts", *Tetrahedron Letters*, vol. 34, No. 37, 5863-66 (1993).

R. J. Vijin et al., Synthesis, 573 (1994).

Davis, "Chemistry Letters", vol. 33, Issue 9, 1072-77 (2004).

Davis et al., "Ionic Liquids in Synthesis", P. Wasserscheid and T. Welton, eds., Wiley-VCH Verlag GmbH & Co. KGaA, Chapter 2 (2002).

M.G. Djamali, P. Burba, K.H. Lieser, "Snythese und Eigenschaften eines Celluloseaustauschers mit Diaminodibenzo-18-Krone-6 als Ankergruppe", Die Angewandte Makromolecular Chemie, vol. 92, 145-54 (1980).

K. Babic, "Reactive and Functional Polymers", vol. 66, 1494-1505 (2006).

Trumbo et al., "Copolymerization Behavior of 3-Isopropenyl-α,α-Dimethylbenzylamine and Preliminary Evaluation of the Copolymers in Thermoset Coatings", *Journal of Applied Polymer Science*, vol. 82, 1030-39 (2001).

T. Giesenberg et al., "Synthesis and Functionalization of a New Kind of Silica Particle." *Agnew. Chem. Int. Ed.*, 43, 5697-5700 (2004).

Zhang et al., "An Investigation of Knoevenagel condensation reaction in microreactors using a new zeolite catalyst", *Applied Catalysis A: General, 261*, 109-118 (2004).

Mehnert et al., "Chemical Communications", 3010 (2002).

Lee and Lee, "Bulletin of the Korean Chemical Society", vol. 25, Issue 10, 1531-37 (2004).

H. R. Snyder and W. E. Hamlin, "Alkylation of Nitroparaffins with Amines and Their Derivatives", *Journal of American Chemical Society*, vol. 72, 5082-85 (1950).

H. G. Johnson, "Reaction of Aliphatic Amines with Formaldehyde and Nitroparaffins. II. Secondary Amines", *Journal of American Chemical Society*, vol. 68, 12-14 (1946).

M. Semkus, "Journal of the American Chemical Society", vol. 68, 10-12 (1946).

Sarac, "Progress in Polymer Science", vol. 24, 1149-1201 (1999).

Brough et al., "Pyrimidinyl Nitronyl Nitroxides", *Chemical European Journal*, vol. 12, 5134 (2006).

Zhou et al., *J. Polym. Sci., Part A Polym. Chem. Ed.*, 29, 1097 (1991).

Mehrotra et al., "Journal of Organometalic Chemistry", vol. 24, 611-21 (1970).

Son et al., "Synthesis of Hexahydro-3,3,5,5,7-pentaalky1-2H-1,4-diazepin-2-ones from 1,3-Diamines and Ketones", *J. Org. Chem.*, vol. 46, 323 (1981).

Senkus, Acetals of Nitro Alcohols and Corresponding Amino Acetals, *J. Amer. Chem, Soc.*, vol. 69, 1380-81 (1947).

Renner et al., "Cure of Epoxy Resins with Esters of Cyanoacrylic Acid", *Journal of Polymer Science: Polymer Chemistry Edition*, vol. 23, 2341 (1985).

Kennedy et al., "Macromers by Carbocationic Polymerization. X. Synthesis, Characterization, and Polymerizability of Cyanoacrylate-Capped Polyisobutylenes", *Journal of Macromolecular Science*, Part A, 28:2, 209-24 (1991).

Khrustalev et al., "Synthesis and X-ray structural study of 1-adamantylmethy 2-cyanoacrylatel and 1,10-decanediol bis-2-cyanoacrylate", *Russian Chemical Bulletin*, vol. 45, No. 9, 2172 (1996).

Y. Gololobov et al., "A novel approach to the synthesis of bis(2-cyanoacrylates)", *Russian Chemical Bulletin*, vol. 42, No. 5, 961 (1993).

Y. Gololobov et al., "Synthesis of bis(2-cyanoacrylates) from 2-cyanoacryloyl chloride and 2-butene-and 2-butyne-1,4-diols", *Russian Chemical Bulletin*, vol. 44, No. 4, 760 (1995).

J.-L. De Keyser et al., "A Versatile and Convenient Multigram Synthesis of Methylidenemalonic Acid Diesters", *J. Org. Chem.*, vol. 53, 4859 (1988).

Vijayalakshmi et al., "Alkyl and substituted alkyl 2-cyanoacrylates. Part I. Synthesis and Properties", *J. Adhesion Science Technology*, vol. 4, No. 9, 733 (1990).

Guseva et al., "Organic Chemistry. Synthesis of functionality substituted cyanoacetates." *Russian Chemical Bulletin*, vol. 42, No. 3, 478 (1993).

Guseva et al., "Organic Chemistry" *Russian Chemical Bulletin*, vol. 43, No. 4, 595 (1995).

Gololobov and Gruber, Russian Chemical Review, vol. 66, Issue 11, 953 (1997).

Senchenya et al., "Silicon-containing esters of α-cyanoacrylic acid: synthesis and properties" *Russian Chemical Bulletin*, vol. 42, No. 5, 909 (1993).

Bowie J. H. et al., "Tetrahedron", vol. 23, 305-20 (1967).

J. S. Norwick et al., J. Org. Chem., 57(28), 7364-66 (1992).

International Search Report for International Patent Application No. PCT/EP2008/064489 dated Dec. 30, 2008.
International Search Report for International Patent Application No. PCT/EP2008/064490 dated May 4, 2009.
International Search Report for International Patent Application No. PCT/EP2008/064488 dated Jul. 16, 2009.
H.C. Haas, et al., "Carbamylmethyl Esthers of Unsaturated Acids"; Journal of Polymer Science; vol. XXXVII, Issue 131; pp. 317-319; 1959, (XP002518680).
J.L. De Keyser et al., "A versatile and convenient multigram synthesis of methylidenamalonic acid diesters", J. Org. Chem., pp. 4859-48562, (1988) (XP002518681).
D.A. Aronovich, et al.; J. Appl. Chem. USSR.; vol. 52, pp. 900-902; 1979 (XP002518682).
X. Yang; Organic Preparations and Procedures International; vol. 30, No. 2; pp. 239-242; 1998 (XP002518684).
P.H. Mason, et al., "A New Route To Substituted Glutaric Acid Derivatives From Allytic Malonates"; Synthetic Communications; vol. 25(2); pp. 183-190; 1995.
T. Sato, et al., "Synthesis of Copper (II) Chelate of ethyl a-(acetoacetoxymethyl)acrylate and its Radical-Initiated Polymerization"; Makromol. Chem., Rapid Commun. vol. 11; pp. 553-557; 1990.
M.L. Meketa, et al., "An Efficacious Method for the Halogenation of β-dicarbonyl Compounds Under Mildly Acidic Conditions"; Tetrahedron Letter; vol. 46(28); pp. 4749-4751; 2005, XP002520970.
M.L. Meketa, et al., "An Efficacious Method for the Halogenation of β-dicarbonyl Compounds Under Mildly Acidic Conditions"; Tetrahedron Letter; vol. 46(28); pp. 4749-4751; 2005, XP002520971.

R.C. Cookson, et al., "2-Phenylthioallyl Alcohols and their Use in the Synthesisi of 1,4-diketones and Cyclopentenones"; Journal of Chemical Society, Chemical Communications: (23); p. 990; 1976, XP002520969.
P.H. Mason, et al., "Some Mechanistic and Synthetic Aspects of the DABCO Catalyzed Rearrangement of Allyllic Esters"; Tetrahedron; vol. 50(41);pp. 12001-12008, XP002520967, (1994).
L.S. Boguslavskaya, et al., Journal of Organic Chemistry; vol. 9; pp. 295-299; 1793, XP002520972.
Samatha, et al., "Effect of Addition of Various Acrylates on the Performance of Ethyl Cyanoacrylate Adhesive", Polym.—Plast. Technol. Eng., 39(2), 381-92, (2000).
Vijayalakshmi, et al., "Synthesis and End Use Evaluation of Pinene-based Alicyclic Acrylates", J. Polym. Mat., 13, pp. 127-131 (1996).
Yamada, et al., "Determination of Absolute Rate Constants for Radical Polymerization and Copolymerization of Ethyl a-Cyanoacrylate in the Presence of Effective Inhibitors against Anionic Polymerization", Makromol. Chem., 184, 1025 (1983).
Vijayalakshmi, et al., "Synthesis of 3-substituted-2-cyanoacrylates: Their Evaluation as Cross-linkers in Cyanoacrylate Adhesive Compositions", J. Polym. Mat., 49, 1387 (1993).
Ponticello, "The Preparation of a-Substituted Acrylic Esters", J. Polym. Sci., Polym. Chem. Edn., 17, pp. 3509-18 (1979).
Pines, Alul and Kolobieski, "Bromination of a-Methylstyrene with N-Bromosuccinimide, Synthesis of 2-Phenyl-1,5-hexadiene", J. Org. Chem., 22, 1113 (1957).

* cited by examiner

EWG = electron withdrawing group

IMINES AND METHODS OF PREPARING ELECTRON DEFICIENT OLEFINS USING SUCH NOVEL IMINES

BACKGROUND OF THE INVENTION

1. Field of the Invention

This invention relates to novel imines, some of which are in the form of ionic liquids ("ILs"), and a process for producing electron deficient olefins, such as 2-cyanoacrylates, using an imine, for instance such novel imines, many of which are in the form of an IL.

2. Brief Description of Related Technology

Cyanoacrylate adhesives are known for their fast adhesion and ability to bond a wide variety of substrates. They are marketed as "super glue" type adhesives. They are useful as an all-purpose adhesive since they are a single component adhesive, very economical as only a small amount will do, and generally do not require any equipment to effectuate curing.

Traditionally, cyanoacrylate monomers have been produced by way of a Krioevenagel condensation react ion between a formaldehyde precursor, such as paraformaldehyde, and an alkyl cyanoacetate with a basic catalyst. During the reaction, cyanoacrylate monomer forms and polymerises in situ to a prepolymer. The prepolymer is subsequently thermally cracked or depolymerised, yielding cyanoacrylate monomer. This approach has remained essentially the same over time, though various improvements and variants have been introduced. See e.g. U.S. Pat. Nos. 6,245,933, 5,624, 699, 4,364,876, 2,721,858, 2,763,677 and 2,756,251.

In U.S. Pat. No. 3,142,698, the synthesis of difunctional cyanoacrylates using a Knoevenagel condensation reaction is described. However, the ability to thermally depolymerise the resulting, now crosslinked, prepolymer in a reliable and reproducible manner to produce pure difunctional monomers in high yields is questionable [see J. Buck, *J. Polym. Sci. Polym. Chem. Ed.*, 16, 2475-2507(1978), and U.S. Pat. Nos. 3,975,422, 3,903,055, 4,003,942, 4,012,402, and 4,013,703].

A variety of other processes for producing cyanoacrylate monomers are known, some of which are described below. For instance, U.S. Pat. No. 5,703,267 defines a process for producing a 2-cyanoacrylic acid which comprises subjecting a 2-cyanoacrylate and an organic acid to a transesterification reaction.

U.S. Pat. No. 5,455,369 defines an improvement in a process for preparing methyl cyanoacrylate, in which methyl cyanoacetate is reacted with formaldehyde to form a polymer that is then depolymerized to the monomeric product, and in which the purity of yield is 96% or better. The improvement of the '369 patent is reported to be conducting the process in a poly(ethylene glycol) diacetate, dipropionate, or dibutyrate, having a number average molecular weight 200-400, as the solvent.

U.S. Pat. No. 6,096,848 defines a process for the production of a biscyanoacrylate, which comprises the steps of esterifying a 2-cyanoacrylic acid or transesterifying an alkyl ester thereof to obtain a reaction mixture; and fractionally crystallizing the reaction mixture to obtain the biscyanoacrylate.

U.S. Pat. No. 4,587,059 defines a process for the preparation of monomeric 2-cyanoacrylates comprising the steps of (a) reacting (i) a 2,4-dicyanoglutarate with (ii) formaldehyde, cyclic or linear polymers of formaldehyde, or a mixture thereof, in the presence of between about 0.5 and about 5 mols of water per mol of 2,4-dicyanoglutarate, at an acid pH of about 3 to slightly less than 7, and at a temperature of about 70 to about 140, to form an oligomeric intermediate product, and (b) removing water that is present from step (a) and thermalizing the oligomeric intermediate product for a period of time sufficient to effect its conversion to monomeric 2-cyanoacrylates.

Commercial production of cyanoacrylate monomers ordinarily relies on the depolymerisation of a prepolymer formed under Knoevenagel condensation reaction conditions, as noted above. Still today the Knoevenagel condensation reaction is believed to remain the most efficient and prevalent commercial method for producing high yields of monofunctional cyanoacrylates. Nevertheless, it would be desirable to not have to resort to thermally induced depolymerisation of a prepolymer produced by the Knoevenagel condensation reaction. This prospect may also enable facile access to highly useful difunctional monomers, such as so-called bis-cyanoacrylates or hybrid materials of cyanoacrylate and other polymerisable or reactive functionality.

Absent from the published literature, however, is the use of imines in the preparation of electron deficient olefins, such as 2-cyanoacrylates. Until now.

SUMMARY OF THE INVENTION

Unlike the state of the technology, the present invention provides a direct, or substantially "crackless", synthesis of electron deficient olefins, such as 2-cyanoacrylate ester monomers, using an imine. Ordinarily, any monomer that may polymerize in the vapour phase is instantly cracked without recourse to isolation of a bulk "prepolymer", as is the case for state-of-the-art commercial cyanoacrylate synthetic methods. Such a situation is referred to as "crack-on-formation".

The imine in some cases may be an imine having an onium salt such as an ammonium or amine salt functionality. In some cases the imines may be termed an "ionic liquid" (or "IL") or a task specific ionic liquid (or, "TSIL"), as will be discussed in more detail below. In other cases the imine may be tethered to a support, as is explained in more detail below.

The imine, which may have an onium salt such as an ammonium or amine salt functionality, may be described as a novel composition of matter embraced within structure I:

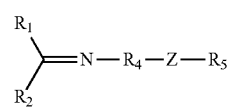

where $R_1$ and $R_2$ are each independently selected from H, alkenyl, or alkynyl; $R_4$ is a tertiary substituted carbon atom two of the substituents of which are each independently selected from linear, branched, or cyclic hydrocarbons, or taken together form a cyclic or polycyclic (as the case may be) structure, which itself may have substituents attached thereto; Z is a spacer that may contain a member selected from linear, branched, or cyclic hydrocarbons, charged or uncharged. N, P or S; and $R_5$ is selected from hydrogen, linear, branched, or cyclic hydrocarbons, or one or more of such hydrocarbons taken together to form a cyclic or polycyclic (as the case may be) structure, which hydrocarbon may have substituents attached thereto or may be interrupted or substituted by a member selected from an inorganic species, an organosilane linkage or group, an organosiloxane linkage or group, a N-contain containing linkage or group, a P-containing linkage or group, or a S-containing linkage or group, or substituted by a member selected from a vinyl group, a (meth) acrylate group, a styryl group or an epoxide group.

The inventive process for the preparation of a reactive electron deficient olefin involves the steps of:
(a) providing:
an imine generally within structure II:

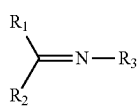

where $R_1$-$R_2$ are each independently selected from H, alkenyl, or alkynyl; and $R_3$ is a hydrocarbon moiety comprising a tertiary carbon which is attached to the N atom, where the tertiary carbon atom is attached to or forms part of one or more substituents selected from linear, branched, or cyclic alkyl or alkenyl groups, or one or more taken together form a cyclic or polycyclic (as the case may be) alkyl or alkenyl structure, which itself (themselves) may have substituents attached thereto; and a compound containing a methylene linkage having at least one electron withdrawing substituent attached thereto, where the electron withdrawing substituent is selected from nitrile, carboxylic acids, carboxylic esters, sulphonic acids, ketones or nitro;

(b) reacting the imine of structure II and the compound under appropriate conditions and for a time sufficient to yield a reactive electron deficient olefin; and (c) optionally separating from the reaction mixture of step (b) the so formed reactive electron deficient olefin to yield the reactive electron deficient olefin; and (d) optionally reacting an amine formed in reaction step (b) and following separation step (c) with formaldehyde or a source thereof to reform the imine of structure II; and (e) optionally repeating steps (b), (c) and (d).

In an alternative aspect, the inventive process involves the preparation of a 2-cyanoacrylate ester, and includes the steps of:

(a) providing as reactants a mixture of formaldehyde or a source thereof and a primary amine having a nitrogen atom attached to a tertiary carbon atom to form an imine generally within structure II;

(b) providing an alkyl cyanoacetate and reacting the imine from step (a) therewith; and (c) optionally separating from the mixture the so-formed 2-cyanoacrylate ester to yield 2-cyanoacrylate ester; and (d) optionally either:
(1) separating from the treatment of step (c) an amine so formed or
(2) separating from the treatment of step (c) an amine so formed and reacting the amine with formaldehyde or a source thereof to form an imine; and (e) optionally repeating steps (c) and (d)

In another alternative aspect, the inventive process involves the preparation of a vinylidene cyanide, and includes the steps of (a) providing as reactants a mixture of formaldehyde or a source thereof and a primary amine having a nitrogen atom attached to a tertiary carbon atom to form an imine generally with in structure II;

(b) providing malononitrile and reacting the imine from step (a) therewith; and (c) optionally separating from the mixture the so-formed vinylidene cyanide to yield vinylidene cyanide; and (d) optionally either:
(1) separating from the treatment of step (c) an amine so formed or
(2) separating from the treatment of step (c) an amine so formed and reacting the amine with formaldehyde or a source thereof to form an e; and (e) optionally repeating steps (b), (c) and (d).

In still another alternative aspect, the inventive process for the preparation of a vinylidene dialkyl malonate, and includes the steps of:

(a) providing as reactants a mixture of formaldehyde or a source thereof and a primary amine having a nitrogen atom attached to a tertiary carbon atom to form an imine generally within structure II;

(b) providing a dialkyl malonate and reacting the imine from step (a) therewith; and (c) optionally separating from the mixture the so-formed vinylidine dialkyl malonate ester to yield vinylidine dialkyl malonate ester; and (d) optionally either:
(1) optionally separating from the treatment of step (c) an amine sc formed or
(2) separating from the treatment of step (c) an amine so formed and reacting the amine with formaldehyde or a source thereof to form an imine; and (e) optionally repeating steps (b), (c) through (d).

In these processes, an imine generally within structure II is used as a reactant to yield the electron deficient olefin. The imine may have an onium such as an ammonium or amine salt functionality, as noted above, and as such may be embraced more specifically within structure I. Alternatively, or additionally, as noted above and discussed in more detail below the imine may be tethered to a support.

In any of these aspects, the synthetic process may be conducted with or without added catalyst. When a catalyst is added, desirably the catalyst should be one that is not a solely basic nucleophile. Thus, an acidic system would be preferred and a ditropic system may be used, as well.

DETAILED DESCRIPTION OF THE INVENTION

Figure 1:
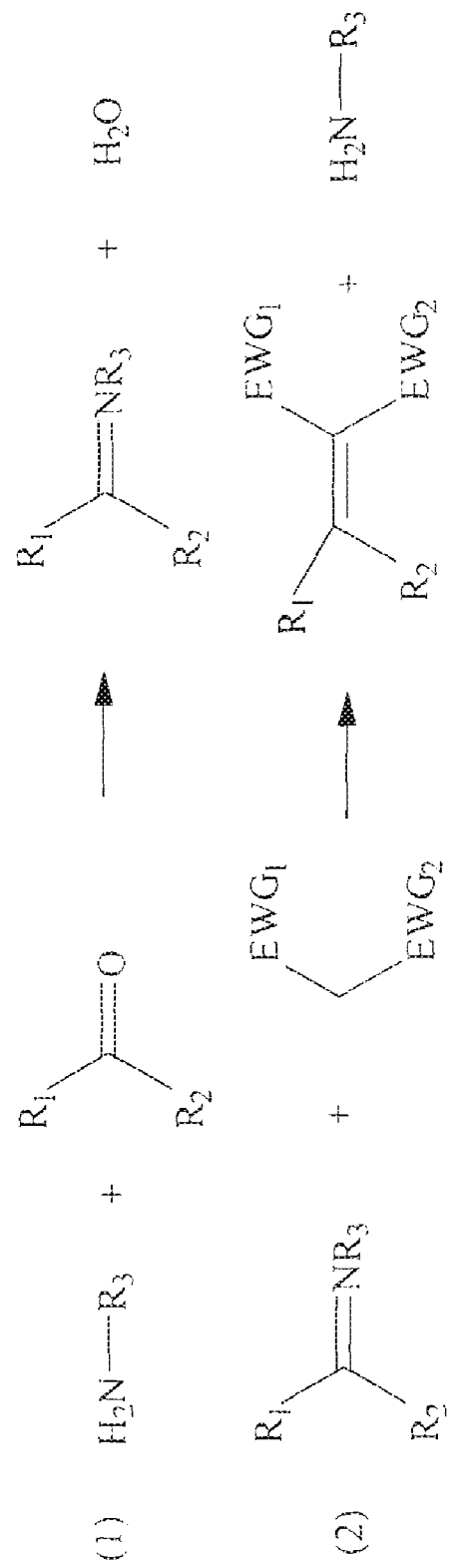
FIG. 1 depicts a general scheme by which electron deficient olefins may be prepared from a t-alkyl imine (shown in the second step), which itself is prepared in the preceding step according to the present invention.

As noted above, the present invention provides among other things a novel composition, embraced by structure I:

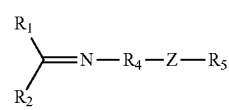

where $R_1$ and $R_2$ are each independently selected from H, alkenyl, or alkynyl; $R_4$ is a tertiary substituted carbon atom two of the substituents of which are each independently selected from linear, branched, or cyclic hydrocarbons, or taken together form a cyclic or polycyclic (as the case may be) structure, which itself may have substituents attached thereto; Z is a spacer that may contain a member selected from linear, branched, or cyclic hydrocarbons, charged or uncharged N, P or S; and $R_5$ is selected from hydrogen, linear, branched, or cyclic hydrocarbons, or one or more of such hydrocarbons taken together to form a cyclic or polycyclic (as the case may be) structure, which hydrocarbon may have substituents attached thereto or may be interrupted or substituted by a member selected from an inorganic species, an organosilane linkage or group, an organosiloxane linkage or group, a N-containing linkage or group, a P-containing linkage or group, or a S-containing linkage or group, or substituted by a member selected from a vinyl group, a (meth)acrylate group, a styryl group or an epoxide group.

The imines (whether with reference to structure I or II) may be in the form of an IL having a melting point less than 100° C., which in its molten form contains only ions. The IL is also not distillable at a pressure of 1 mBar and a temperature of 100° C. The IL is in the liquid state at a temperature in the range of –10° C. to +250° C., such as in the range of 15° C. to +250° C., desirably in the range of 50° C. to +150° C.

In one aspect, the inventive process for the preparation of a reactive electron deficient olefin involves the steps of:
(a) providing:
an imine within structure II:

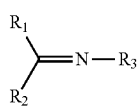

II where $R_1$-$R_2$ are each independently selected from H, alkenyl, or alkynyl; and $R_3$ is a hydrocarbon moiety comprising a tertiary carbon which is attached to the N atom, where the tertiary carbon atom is attached to or part of one or more substituents selected from linear, branched, or cyclic, or one or more together form a cyclic or polycyclic (as the case may be) structure, which itself (themselves) may have substituents attached thereto; and
   a compound containing a methylene linkage having at least one electron withdrawing substituent attached thereto, where the electron withdrawing substituent is selected from nitrile, carboxylic acids, carboxylic esters, sulphonic acids, ketones or nitro;
(b) reacting the imine of structure II and the compound under appropriate conditions and for a time sufficient to yield a reactive electron deficient olefin; and
(c) optionally separating from the reaction mixture of step (b) the so formed reactive electron deficient olefin to yield the reactive electron deficient olefin; and
(d) optionally reacting an amine formed in reaction step (b) and following separation step (c) with formaldehyde or a source thereof to reform the imine of structure II; and
(e) optionally repeating steps (b), (c) and (d).

In an alternative aspect, the inventive process involves the preparation of a 2-cyanoacrylate ester, and includes the steps of:
(a) providing as reactants a mixture of formaldehyde or a source thereof and a primary amine having a nitrogen atom attached to a tertiary carbon atom to form an imine generally within structure II;

(b) providing an alkyl cyanoacetate and reacting the imine from step (a) therewith; and
(c) optionally separating from the mixture the so-formed 2-cyanoacrylate ester to yield 2-cyanoacrylate ester; and
(d) optionally either:
   (1) separating from the treatment of step (c) an amine so formed or
   (2) separating from the treatment of step (c) an amine so formed and reacting the amine with formaldehyde or a source thereof to form an imine; and
(e) optionally repeating steps (b), (c) and (d).

In another alternative aspect, the inventive process involves the preparation of a vinylidene cyanide, and includes the steps of:
(a) providing as reactants a mixture of formaldehyde or a source thereof and a primary amine having a nitrogen atom attached to a tertiary carbon atom to form an imine generally within structure II;
(b) providing malononitrile and reacting the imine from step (a) therewith; and
(c) optionally separating from the mixture the so-formed vinylidene cyanide to yield vinylidene cyanide; and
(d) optionally either:
   (1) separating from the treatment of step (c) an amine so formed or
   (2) separating from the treatment of step (c) an amine so formed and reacting the amine with formaldehyde or a source thereof to form an imine; and
(e) optionally repeating steps (b), and (d).

In still another alternative aspect, the inventive process for the preparation of a vinylidene alkyl malonate, and includes the steps of:
(a) providing as reactants a mixture of formaldehyde or a source thereof and a primary amine having a nitrogen atom attached to a tertiary carbon atom to form an imine generally within structure II;
(b) providing a dialkyl malonate and reacting the imine from step (a) therewith; and
(c) optionally separating from the mixture the so-formed vinylidine dialkyl malonate ester to yield vinylidine dialkyl malonate ester; and
(d) optionally either.
   (1) separating from step (c) an amine so formed or
   (2) separating from step (c) an amine so formed and reacting the amine with formaldehyde or a source thereof to form an imine; and
(e) optionally repeating steps (b), (c) and (d).

In any of these aspects, the synthetic process may be conducted with or without added catalyst, as noted above.

The novel imines embraced by structure I are useful in the preparation of electron deficient olefins, and if desired the novel imine used in the process may be reformed from a byproduct of the reaction. These novel imines have substantially zero vapour pressure as noted above may be designed so that they are not distillable at a pressure of 1 mBar and a temperature of 100° C., whereas the electron deficient olefins are volatile and may be isolated by direct vacuum distillation from the reaction vessel. Further, the original amine used to form the novel imine may be recovered or reacted with a source of formaldehyde to reform the novel imine.

Reference to the figures may be useful to appreciate further the present invention, which is described in more detail below and in the Examples section that follows below.

Figure 2:
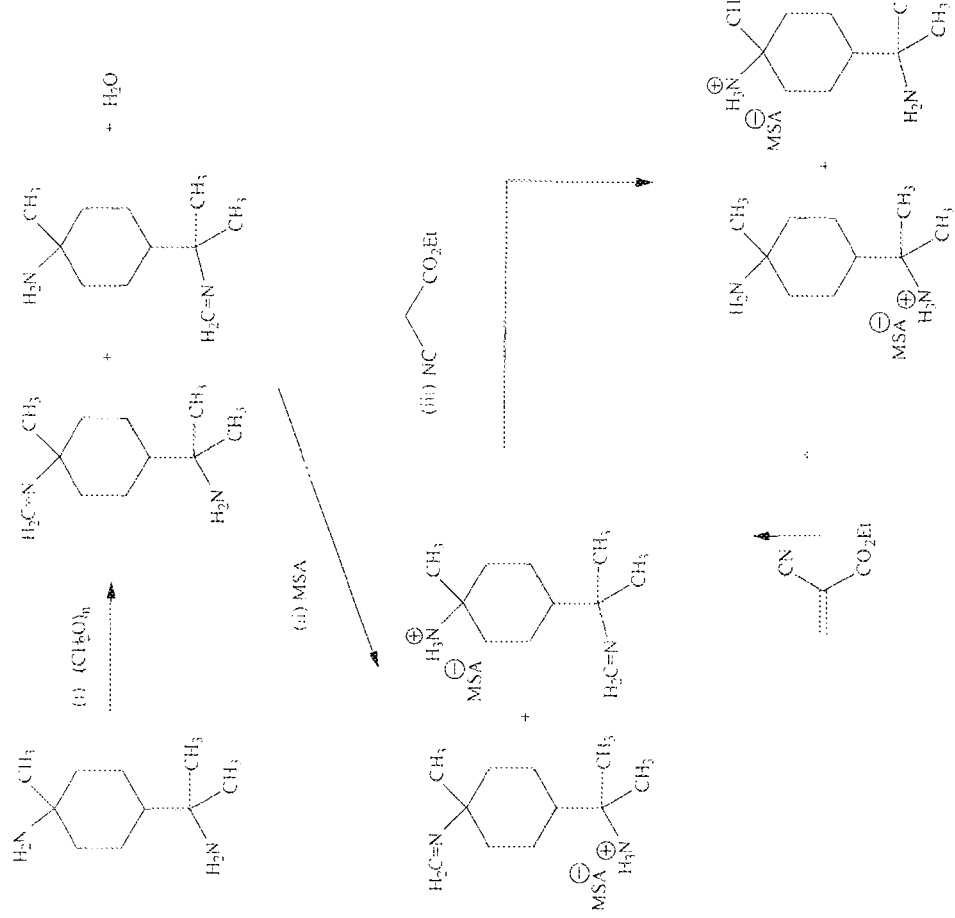
FIGS. 2, 3 and 4 depict synthetic schemes by which 2-cyanoacrylate esters may be prepared from t-alkyl imines [having ammonium (FIG. 2) imidazolium (FIG. 3) or pyrrolidinium salt (FIG. 4) functionality as well], according to the present invention.

Thus, with reference to FIG. 1, as an initial reactant, is an aldehyde compound having the structure $R_1R_2C=O$, where $R_1$ is hydrogen and $R_2$ is a hydrogen, vinyl or propargyl. The aldehyde compound may be an aldehyde itself or a source of an aldehyde, such as one that yields an aldehyde like formaldehyde under appropriate reaction conditions. The aldehyde compound in a desirable embodiment includes formaldehyde (or a source thereof, such as paraformaldehyde, formalin, or 3,5-trioxane) or vinyl aldehydes, such as acrolein. In FIG. 2, paraformaldehyde is shown as $(CH_2)_n$, where n>1.

As a reactant with such an aldehyde is a primary amine. Primary amines attached to a carbon bearing no alpha protons are particularly desirable, such as t-alkyl primary amines. Rohm and Haas Co., Philadelphia, Pa. has sold commercially for a number of years a series of t-alkyl primary amines, which are designated as PRIMENE-brand amines, For instance, t-alkyl primary amines available from Rohm and Haas include PRIMENE 81-R and PRIMENE JM-T. These PRIMENE-brand t-alkyl primary amines have highly branched alkyl chains in which the amino nitrogen atom is attached directly to a tertiary carbon. These t-alkyl primary amines consist of mixtures of isomeric amines, with PRIMENE 81-R consisting of an isomeric mixture with $C_{12}$-$C_{14}$ carbon branches and having an average molecular weight of 185 and PRIMENE JM-T consisting of an isomeric mixture with $C_{16}$-$C_{22}$ carbon branches and having average molecular weight of 269.

PRIMENE MD, also known as menthanediamine (1,8-diamino-p-menthane) or (4-amino-α,α-4-trimethyl-cyclohexanemethanamine, CAS No. 80-52-4), is a primary alicyclic diamine, in which both amino groups are attached to tertiary carbon atoms. Like other t-alkyl primary amines, menthanediamine is somewhat less reactive than similar straight chain diamines. Yet another PRIMENE, PRIMENE TOA has tertiary alkyl chains and a molecular weight of 129.

In FIG. 1 equation (2) if $EWG_1$ is nitrile and $EWG_2$ is acetate, for instance, cyanoacrylic ester is formed with a primary amine as a byproduct. When the primary amine byproduct is volatile (e.g., t-butyl amine), volatile electron deficient olefinic monomer (e.g., ethyl cyanoacrylate) which forms during the exothermic reaction and under the conditions employed (e.g., addition of heat and vacuum) is incompletely removed from the reaction mixture, for example by vacuum distillation, before the primary amine byproduct initiates polymerization of the monomer.

However, if the initial imine molecule used in the reaction is itself designed to substantially non-volatile under the conditions employed so that the byproduct primary amine derived therefrom and after reaction with an active methylene compound, such as a cyanoacetate, the volatile electron deficient olefinic monomer may be separated from the reaction mixture without subsequent initiation by the primary amine byproduct. In this situation, for instance, the optional separation step of the inventive processes may be performed.

Various methods may be considered to render an imine molecule and the primary amine byproduct, formed after reaction with an active methylene compound, substantially non-volatile under the conditions employed. Such molecular design methods to control volatility of the byproduct primary amine include making the resulting byproduct amine form part of (i) an ionic liquid or supported ionic liquid system that is non-stillable and has a near zero vapour pressure, (ii) a macromolecule that does not co-distill with volatile target electron deficient olefins, (iii) a system that is tethered to a solid support, and (iv) a system where the imine molecule and subsequently formed primary amine byproduct is sorbed within a macroporous support (e.g., PRIMENE JM-T having been included in porous substrates for reaction with aldehydes; see K. Babic, et al., *Reactive and Functional Polymers*, 66, 1494 (2006)).

In case (i) for example the imine may be a functionality within an ionic liquid such as a so-called "Task Specific ionic Liquid", or "TSILs". See e.g. International Patent Publication No. WO 03/086605 A2, where TSILs are described. See also Davis, *Chem Letts.*, 33(9), 1072 (2004). If the molecule bearing an imine function of and a charged species is itself non-volatile under the conditions employed yet not an ionic liquid itself, it may be solvated in an ionic liquid, such as those commercially available from Merck, BASF, IoLoTec, and Solvent Innovation, for instance.

In case (ii), Trumbo et al., *J. Appl. Polym. Sci.*, 82, 1030 (2001) describe, for example, the preparation and copolymerisation of the 3-isopropenyl, alpha, alpha-dimethylbenzylamine monomer. Imines are reaction products of carbonyl-containing compounds and amines. General methods of simple imine formation are described for instance in R. J. Vijin et al., *Synthesis*, 573 (1994) and U.S. Pat. Nos. 2,582,128 and 5,744,642. Thus, a t-alkylimine may be prepared from the 3-isopropenyl, alpha, alpha-dimethylbenzylamine monomer by reaction with formaldehyde or a source of formaldehyde. The monomer thus formed may be used in the construction of polymers or copolymers bearing t-alkyl imine functionalities by polymerizing said monomer or conducting polymer analogous reactions, where the vinyl function in the monomer reacts with active sites on preformed polymers, for example by hydrosilylation or thiol-ene reactions that are well known to those skilled in the art.

In case (iii) the use of functionalised silica particles is well known in industry, for example, through the use of silane coupling agents bearing reactive groups. Additionally so-called chlorosiloxane ("CSN") particles are known in which the silica particles bear a Cl functionali that may react directly with a variety of groups such as OH. [See T. Giesenberg, et al., *Agnew Chem. Int. Ed.*, 43, 5697 (2004); European Patent Application No. EP 03024279.6 and references therein]. Zeolites with surface grafted primary amines (but not attached to tertiary carbons) have been used as catalysts for the Knoevenagel reaction between ethylcyanoacetate and benzaldehyde [Mang et al., *Applied. Catalysis A: General*, 261, 109 (2004)].

In case (iii) so-called solid supported ionic liquids may be used [see Mehnert et al., *Chem. Commun.*, 3010 (2002)].

In case (iv) t-alkyl amines may be sorbed within a macroporous support [for example, PRIMENE JM-T has been included in porous substrates for reaction with aldehydes; see K. Babic, et al., *Reactive and Functional Polymers*, 66, 1494 (2006)]. Since the PRIMENE JM-T amine also reacts with formaldehyde or a source thereof, then the t-alkyl imine may also be thus immobilized.

Versions of imine ammonium salts derived from PRIMENE MD (structure III) after condensation with paraformaldehyde are shown below in structures IV(a) and IV(b). Such imine ammonium salts possess a structure, in which there exists an imine nitrogen attached to a tertiary carbon, and a quaternary ammonium salt in the same molecule. When X is methane sulfonate, for instance, the mixture of isomeric imine ammonium salts is liquidus at room temperature.

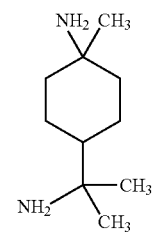

III

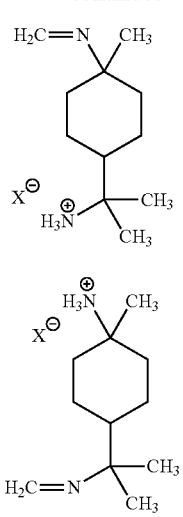

IV(a)

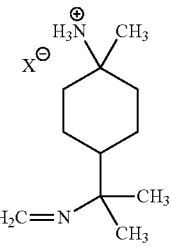

IV(b)

In the case of imines bearing an amine functionality as well, the amine functionality may be converted into ammonium salts embraced by structure I, respectively, by contacting them with an acidic species, such as trifluoroacetic acid, acetic acid, sulphuric acid, methane sulfonic acid, benzene sulfonic acid and camphor sulfonic acid [see e.g. J. March at 802, and references cited therein; see also M. B. Smith, Organic Synthesis, McGraw Hill International, Chemistry Series, 1302 (1994) and references cited therein and Abbaspour Tehrani and De Kimpe, Science of Synthesis, 27, 313 (2004), and references cited therein]. When there is more than one basic functionality in the same molecule further mixtures may result, for example, in the above case, iminium salts may also form.

Molecular design may be used to regenerate the original imines after reaction. For instance, molecules with imines that also bear ammonium salts will yield primary amines as byproducts. The latter may be water soluble and subsequently reacted with aqueous formaldehyde to reform imines molecules also bearing ammonium salt structures for example.

As noted above, the present invention provides novel imines embraced by structure I

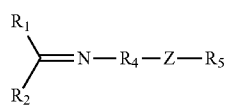

I where $R_1$-$R_2$ are each independently selected from H, alkenyl, or alkynyl; $R_4$ is a tertiary substituted carbon atom, two of the substituents of which are each independently selected from linear, branched, or cyclic hydrocarbons, or taken together form a cyclic or polycyclic (as the case may be) structure, which itself may have substituents attached thereto; Z is a spacer that may contain a member selected from linear, branched, or cyclic hydrocarbons, charged or uncharged N, P or S; and $R_5$ is from hydrogen, linear, branched, or cyclic hydrocarbons, or one or more of such hydrocarbons taken together to form a cyclic or polycyclic (as the case may be) structure, which hydrocarbon may have substituents attached thereto or may be interrupted or substituted by a member selected from an inorganic species, an organosilane linkage or group, an organosiloxane linkage or group, a N-containing linkage or group, a P-containing linkage or group, or a S-containing linkage or group, or substituted by a member selected from a vinyl group, a (meth)acrylate group, a Styryl group or an epoxide group.

More specific examples of such novel imines within structure I include those where each of $R_1$-$R_2$ are independently H, vinyl or propargyl, $R_4$ is a tertiary substituted carbon atom, two of the substituents of which are methyl, Z contains a charged N to which is associated X, where X is a non-nucleophilic and/or acidic anion, such as $PF_6$, $BF_4$, $AsF_6$, $SbF_6$, $Tf_2N$, $(CN)_2N$, triflate, camphorsulfonate, benzenesulfonate, saccharinate, acesulfamate, $MF_6$, where M is Nb or Ta, nitrate, $CF_3CO_2$, halide, phosphate, perchlorate or $CH_3SO_3$, the latter of which may be the same or different to the anion counterbalancing charge for the organic cation. See also Davis et al. in *Ionic Liquids in Synthesis*, P. Wasserscheid and T. Welton, eds., Wiley-VCH Verlag GmbH & Co. KGaA, Chapter 2 (2002). (See e.g. International Patent Publication No. WO 03/086605 A2.)

$R_5$ is an alkyl group, such as methyl, ethyl, propyl or butyl, and aromatic or substituted aromatic group, such as phenyl or substituted phenyl, alicyclic group, such as cyclohexyl group, a polymerisable group, such as an acrylate group, vinyl group, a scyryl group or an epoxide group.

Examples of such imines within structure I are shown below, as structures V-XI.

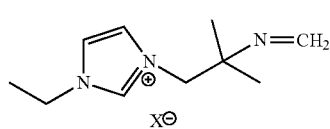

V

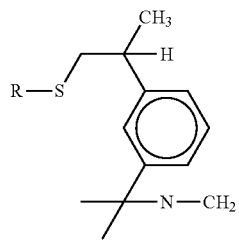

VI

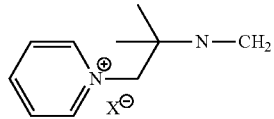

VII

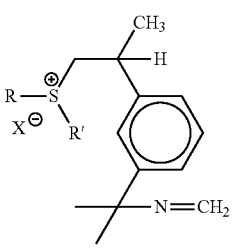

VIII

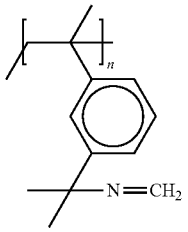

IX

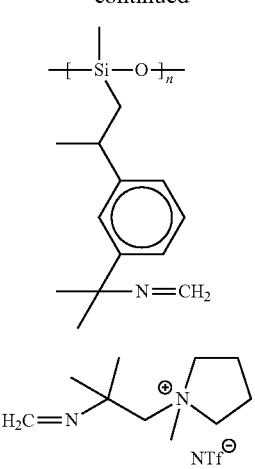

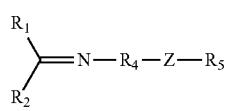

Phosphonium-containing ionic liquids are described for example in International Patent Publication No. WO 0187900.

In another aspect, the composition of matter that embraces novel imines may be tethered to a support. That is, with reference to structure I $R_5$ may be linked to or be part of a support material.

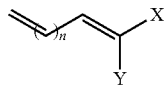

$R_1$-$R_2$ and $R_4$ are as defined above; Z here is a linker (having a functional group capable of reacting with $R_5$) and may contain atoms or groups selected from O, ester, reverse ester, S, thioester, reverse thioester, amide, reverse amide, urea, urethane, and reverse urethane; and $R_5$ is a support capable of reacting with a functional group to form Z. For instance, the support may be a solid support such as zeolite, silica, aluminum oxide, and derivatives thereof, or a quid support such as a liquid polymer having one or more functional groups. The functional groups on the support may react to form the linker, as exemplified above. Illustrative examples of some polymers are referred to in structures V and XI, for example, where n in those structures is between 10 and 70.

The imines, whether or not bearing ammonium salt functionality or whether or not they are tethered to a support, are then reacted with compounds containing a methylene linkage having at least one, desirably two, electron withdrawing substituent(s) attached thereto. In these compounds, the electron withdrawing substituent is selected from nitrile, carboxylic acids, carboxylic esters, sulphonic acids, ketones or nitro. In a desirable embodiment, these compounds have two or more electron withdrawing substituents, which may be the same or different, such as nitrile and carboxylic acid ester—in this case, a cyanoacrylate. Of course, the reactivity of these compounds in large part depends on the degree of electron withdrawing capability of the particular substituent, and the number of substituents on the active methylene carbon.

Representative examples of these compounds include malononitrile, malonic acid and its esters, ethyl nitroacetate, cyanoacetic acid and its esters, 4-cyclopentene-1,3-dione, cyclopentane-1,3-dione, 4-cyclohexene-1,3-dione, cyclohexane-1,3-dione, 2,2-dimethyl-1,3-dioxane-4,6-dione (Meldrum's acid), and tetronic acid, some of which are commercially available for instance from The Aldrich Chemical Co. A particularly desirable example is the ethyl ester of cyanoacetic acid.

Structure XII below illustrates the electron deficient olefinic products that would result from a reaction with imine, using the above reactants.

Here, when a source of formaldehyde is used, n is 0 in structure XII and a methylenic compound results with X and Y being nitrile, carboxylic acid, carboxylic acid esters; X being nitro and Y being carboxylic acid ester; or X being nitrile and Y being carboxylic acid ester, the latter combination giving rise to 2-cyanoacrylates using alkyl cyanoacetates as a substrate, for example. When acrolein is used, is 1 and the same combinations of X and Y can apply in structure XII.

The electron deficient olefin so formed by the inventive processes may be a variety of olefins having at least one electron withdrawing group attached thereto. In a desirable embodiment, as noted above with respect to the second reactant, the electron deficient olefin so formed will have two or more electron withdrawing groups attached thereto, which may be the same or different. Particularly desirable products have two electron withdrawing groups attached thereto that are different, such as 2-cyanoacrylate esters.

Representative examples of 2-cyanoacrylate esters so formed by the inventive processes include methyl, ethyl, n-propyl, 1-propyl, propargyl, n-butyl, i-butyl, n-pentyl, n-hexyl, 2-ethylhexyl, n-octyl, n-nonyl, oxononyl, n-decyl, n-dodecyl, allyl, ethynyl, 2-butenyl, cyclohexyl, phenyl, phenethyl, tetrahydrofurfuryl, chloroethyl, 2,2,2-trifluoroethyl, hexafluoroisopropyl, methoxymethyl, methoxyethyl, methoxybutyl, ethoxyethyl, propoxyethyl, butoxymethyl, butoxyethyl and dimethyl siloxane esters of 2-cyanoacrylic acid.

The electron deficient olefin may also be a compound having one end terminating with a cyanoacrylate, cyanopentadienoate, or alkylene derived from dimalonate or malononitrile and another end terminating with a group selected from branched and unbranched alkyl esters, esters containing aromatics and heterocylic nuclei, acrylates, cyanoacrylates, siloxanes, blocked and unblocked isocyanates, anhydrides, silanes, vinyls, and acetylenes.

The reaction of the inventive processes may proceed with or without heating or cooling, depending of course on the specific reactants and the scale of the reaction. Decomposition of the source of formaldehyde, e.g., paraformaldehyde, may occur under gentle heating up to a temperature of about 70° C., to liberate formaldehyde in situ in the reaction medium. The temperature may be reached through an external heating element or internally by means of the exotherm that may be generated, depending of course on the identity of the reactants. The temperature of the reaction should be controlled however to accommodate any such exothermic processes.

The time of reaction may be monitored by reference to the formation of the desired electron deficient olefin product. A $^1$H NMR spectrometer is a particularly useful tool in this regard. The time of reaction may be as little as 1 minute, for instance, or longer or shorter for that matter depending again on the identity of the specific reactants, the scale of the reaction and whether heat is introduced to or removed from the reaction conditions.

Once formed, the electron deficient olefin may be isolated by direct distillation under vacuum out the reaction mixture or by freezing it in a solid form and separating off the liquid phase. The former method is particularly desirable in the case of 2-cyanoacrylates (particularly their lower esters) which may be relatively volatile.

The electron deficient olefin so formed by the inventive processes may be stabilized during the synthesis and/or isolation procedure, and also in the isolated product to improve its shelf life. Suitable stabilizers include free radical stabilizers and acidic stabilizers.

For example, free radical stabilizers include hydroquinone, pyrocatechol, resorcinol or derivatives thereof, such as hydroquinone monoethyl ether, or phenols, such as di-t-butylphenol or 2,6-di-t-butyl-p-cresol, 2,2'-methylene-bis-(4-methyl-6-t-butylphenol), bisphenol A, dihydroxydiphenylmethane, and styrenized phenols.

For example, acidic stabilizers include sulfuric acid, hydrochloric acid, sulfonic acids, such as methane, ethane or higher sulfonic acids, p-toluene sulfonic acid, phosphoric acid or polyphosphoric acids, silyl esters of strong acids, such as trialkyl chlorosilanes, dialkyl dichlorosilanes, alkyl trichlorosilanes, tetrachlorosilane, trialkyl silylsulfonic acids, trialkyl silyl-p-toluene sulfonates, bis-trialkyl silylsulfate and trialkyl silylphosphoric acid esters.

The amount of either stabilizer used to stabilize the electron deficient olefin prepared by the inventive processes is well known to those of ordinary skill the art, and may be varied depending on the properties of the resulting composition made from the so formed electron deficient olefin.

The following examples are intended to illustrate but in no way limit the present invention.

EXAMPLES

PRIMENEs TOA, 81-R and JM-T were used to prepare imines by reaction of the amines with stoichiometric equivalents of paraformaldehyde and removal of water of condensation. All imines formed were distillable liquids and existed in stable monomeric imine forms as confirmed by $^1$H NMR 60 MHz (CDCl$_3$) 2H D 7.16, 7.09 ppm, (TOA imine); 2H s (br) 7.45 ppm (81-R imine) and (CD$_3$COCD$_3$) 2H 6.86 PPM (JM-T imine) and FTIR (1650 cm$^{-1}$ for each).

Example 1

A two necked flask was configured for vacuum distillation, with one side neck of the flask plugged with a rubber septum through which PRIMENE TOA imine (from above) was placed therein. A vacuum of I mbar was thereafter applied with stirring. When any out-gassing had subsided from the stirred PRIMENE imine, ethyl cyanoacetate was injected at room temperature through the rubber septum directly into PRIMENE TOA imine at a 20 mmol level and a ratio of 1:1.1. The reaction between the two reactants was observed to very exothermic. Ethyl cyanoacrylate monomer polymerised in the condenser of the distillation apparatus to give a thick coating of a cream coloured brittle polymer. FTIR analysis (KEr) of that cream coloured brittle polymer showed the presence of a weak ON stretch at approximately 2250 cm$^{-1}$ and a strong carbonyl ester at approximately 1750 cm$^{-1}$, each consistent with polyethyl cyanoacrylate.

Example 2

When malononitrile was used in place of ethyl cyanoacetate in Example 1, the reaction was extremely vigorous and the resulting brittle polymer was partially charred.

Example 3

When dimethyl malonate was used in place of ethyl cyanoacetate in Example 1, the reaction was less vigorous than the reactions performed in either Examples 1 or 2. Carbonyl ester stretches were observed in the FTIR spectrum, indicating formation of polydimethyl malonate.

Example 4

Reference to FIG. 2 may be helpful. One equivalent of paraformaldehyde in prill form was admixed with PRIMENE MD. The reaction mixture was maintained close to room temperature by cooling if necessary on an ice bath. The mixture was stirred until all the solid paraformaldehyde disappeared. Then, the mixture was heated for one hour at a temperature of 60° C. Water was removed from the mixture by addition of anhydrous sodium sulfate.

The half imine of PRIMENE MD so-formed was reacted with stirring one equivalent of methane sulfonic acid, while maintaining the temperature of the mixture at approximately room temperature. A viscous material resulted that solidified into a cream to slightly yellowish solid. The solid so-formed was soluble in water and was dissolved for purification. The yellow aqueous solution was extracted with dichloromethane to remove unreacted PRIMENE MD. Following extraction, the aqueous solution was evaporated to yield a yellowish solid. The FTIR spectrum of a film cast from dichloromethane onto a NaCl plate showed characteristics of an ammonium salt (broad absorption around 3400 cm$^{-1}$) and a free imine (sharp band at 1650 cm$^{-1}$) The solid was solubilised hot methanol to which some activated charcoal was added. The solution was filtered and evaporated to yield an amorphous mass.

One equivalent of the half-imine half-ammonium methane sulfonate is dissolved in 10 mls of methyl imidazolium hexafluorophoshpate (commercially available from IoLo-Tech Gmbh). The solution is heated and maintained at a temperature of about 100-150° C. in the pot of a fully assembled distillation apparatus, the pot having an additional neck lugged with a rubber septum. The apparatus is maintained under a reduced pressure of 1 mbar. One equivalent of ethyl cyanoacetate, held in a syringe, is injected in one lot through the septum and into the hot reaction medium. Volatile ethyl cyanoacrylate monomer is collected by direct distillation from this mixture as confirmed by $^1$H NMR analysis.

Example 5

Figure 3:
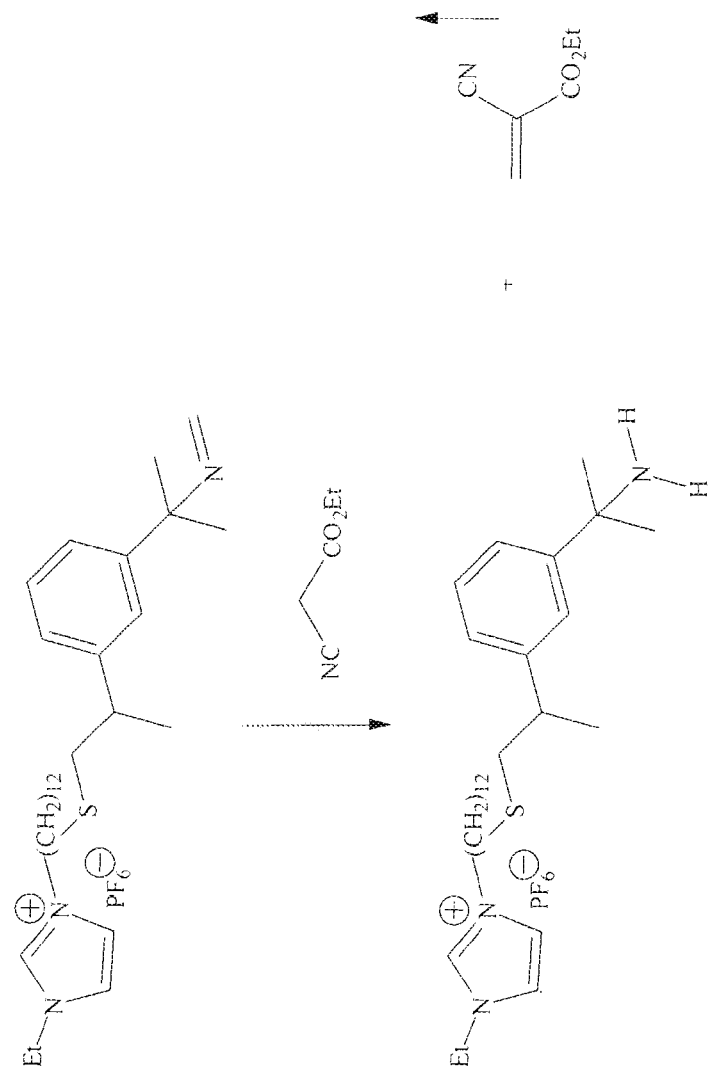

Reference to FIG. 3 may be helpful. 3-Isopropenyl-alpha, alpha-dimethylbenzylamine ("IDBA") was prepared from 3-isopropenyl-alpha, alpha-dimethylbenzyl isocyanate (commercially available from Aldrich Chemical Co.) following the procedure of Trumbo et al., *J. Appl. Polym. Sci.*, 82, 1030 (2001). IDBA was observed to have a boiling point of 93° C. at 1 mm Hg.

A thiol-functionalised ionic liquid, 1-(12 mercaptododecyl)-3 ethyl imidazolium hexafluorophosphate ("EMDIM PF$_6$"), was prepared following the procedure of Lee and Lee, *Bull. Korean Chem. Soc.*, 25(10), 1531 (2004), except that degassed solvents were used during and after hydrolysis of thioacetate. EMDIM $PF_6$ was prepared reversing the hydrolysis and exchange steps cited by Lee and Lee. Thus, the thioacetate-IL.Br was first, exchanged to give thioacetate-IL.$PF_6$ and then the hydrolysis was performed with degassed solvents. Acidification was carried out with $HPF_6$ (aqueous solution, 60%).

One equivalent of IDEA is reacted with one equivalent of EMDIM PF6 in the presence of a small quantity of benzoyl peroxide. The reaction is continued by heating to a temperature of 100° C. until the isopropenyl double bond signal disappears. The reaction product is heated under reflux with one equivalent of paraformaldehyde in benzene until all the solids have disappeared. Water is removed by trapping in a Dean Stark apparatus.

The product from the reaction above is placed in a distillation pot with a side neck and assembled for vacuum distillation. The contents of the distillation pot are held at a temperature of about 100-150° C. and at 1 mbar reduced pressure. The side neck on the pot is plugged with a rubber septum. One equivalent of ethyl cyanoacetate is injected through the septum into the distillation pot and into the imine-imidazole salt. Ethyl cyanoacrylate is distilled directly from the reaction mixture.

Example 6

Figure 4:
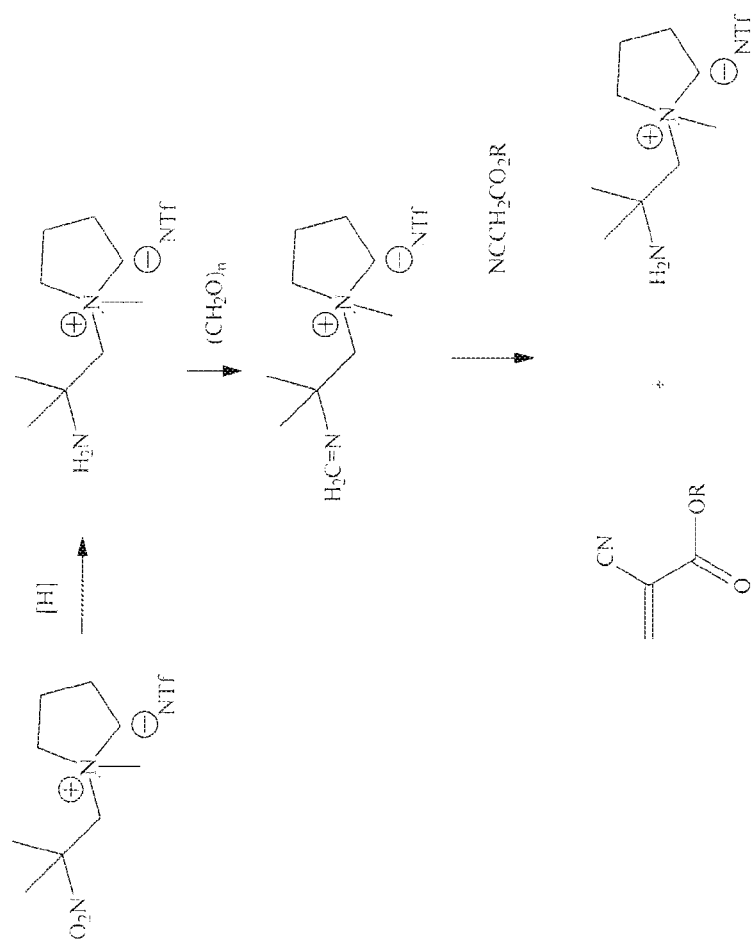

Reference to FIG. 4 may be helpful.

Here, N-(2-methyl-2-nitro-propyl)-pyrrolidine was prepared using the procedure of H. R. Snyder and W. E. Hamlin, *J. Am. Them. Soc.*, 72, 5082-5085 (1950). See also H. G, Johnson, *J. Am. Chem. Soc.*, 68, 12-14 (1946). In a typical preparation, pyrrolidine (100 mls, 1.2 mol) was added with stirring and under ice bath cooling conditions to deionised water (100 mls). To this cooled and stirred mixture was added drop wise 37% aq. formaldehyde (90 mls, 1.2 mol) dissolved in deionised water (100 mls). An exotherm was observed and the temperature of the reaction mixture during the addition was kept below 20° C. When the addition was complete, the reaction mixture was stirred for a period of time of 1 hour, after which time nitropropane (108 mls, 1.2 mol) was added in portions over a period of time of 5 minutes.

This mixture was stirred for a period of time of 16 hours, after which time, on standing, the reaction mixture became a biphasic system with a light green organic layer collecting on the top. The aqueous layer was saturated with sodium chloride and the organic layer was separated, dried with anhydrous sodium sulphate and isolated as a residue. Distillation of the residue (0.7 mbar, 60° C.) resulted in lime green liquid (164 g, 80% yield). FTIR: (film, $cm^{-1}$) 2969, 2876, 2796, 1541, 1462, 1401, 1371, 1344, 1304, 1237, 1202, 1145, 1110, 1020, 990, 905, 858, 820, 557. $^1$H NMR (60 MHz, $CDCl_3$, 1% TMS v/v, ppm) 1.9-1.6 (overlapped singlet and multiplet 10H), 2.6 (t, 4H) 3.0 (s, 2H). CC-MS: retention time 4.44 mins, m/z=84, 100%. Mass spectrum: $C_8H_{16}N_2O_2$, $M_w$=172, 172 ($M^+$), 126 ($M^+$—$NO_2$) 84 ($M^+$-$C_3H_6NO_2$, 100%).

Example 7

Here, N-methyl-N-(2-methyl-2-nitro-propyl)-pyrrolidinium iodide was prepared by dissolving N-(2-methyl-2-nitro-propyl)-pyrrolidine (70 g, 0.4 mol) in toluene (100 mls), and thereafter under ice bath conditions adding drop wise methyl iodide (58 g, 26 mls, 0.41 mol) in toluene (70 mls) over a period of time of 30 minutes. After the addition was complete, the ice bath was removed and the solution was heated to a temperature of 80° C. A white solid was observed to precipitate. Stirring and heating were continued for an additional period of time of 6 hours. The white precipitate was recovered by filtration, and thereafter washed first with acetone (100 mls) and then with diethyl ether (50 mls) to yield after air drying 83 grams (65%), FTIR: (KBr, $cm^{-1}$) 3026, 2978, 2874, 1544, 1492, 1475, 1459, 1439, 1377, 1344, 1307, 1229, 1195, 1152, 1052, 1012, 997, 926, 852, 833. $^1$H NMR (60 MHz, $CDCl_3$/DMSO-$d_6$, ref TMS, ppm) 1.85 (s, 6H) 2.1-2.3 (m, br, 4H) 2.96 (s, 2H) 3.9-3.7 (m, br, 4H) 4.45 (s, 3H). Elemental Analysis: $C_9H_{19}N_2O_2I$, $M_w$=314.16; % C, H, N (theory): 34.41, 6.09, 8.92, respectively; % C, H, N (found): 34.35, 6.01, 8.80, respectively.

Example 8

Here, N-methyl-N-(2-methyl-2-nitro-propyl)-pyrrolidinium bis(trifluoromethylsulfonimide) was prepared by suspending N-methyl-N-(2-methyl-2-nitro-propyl)-pyrrolidinium iodide (83 g, 0.26 mol) with stirring in deionised water (100 mls). To this suspension was added with stirring an aqueous solution of lithium bis-trifluoromethanesulfonimide (75 g, 0.26 mol). Dichloromethane was added to yield a bi-phasic system, which was stirred for a period of time of 2 hours.

The dichloromethane layer was separated, washed with five 50 ml portions of water, and dried over anhydrous sodium sulphate. Solvent was removed under reduced pressure to furnish a light yellow liquid in a yield of 83 grams (69%). This liquid was dried on a vacuum pump (80° C., 0.4 mbar, 5 hours). FTIR: (KBr, $cm^{-1}$) 3003, 2886, 1553, 1480, 1460, 1427, 1394, 1346, 1184, 1139, 1056, 997, 971, 936, 891, 855, 790, 763, 740, 654, 617, 571, 514. $^1$H NMR (60 MHz, $CDCl_3$ 1% TMS v/v) 1.77 (s, 6H), 2.1-2.3 (m, br, 4H), 2.87 (s, 3H), 3.4-3.7 (m, br, 4H), 4.09 (s, 2H).

Example 9

Here, N-methyl-N-(2-amino-2-methyl-propyl)-pyrrolidinium bis(trifluoromethylsulfonimide) is prepared by subjecting N-methyl-N-(2-methyl-2-nitro-propyl)-pyrrolidinium bis(trifluoromethylsulfonimide) from Example 8 to solid supported catalytic hydrogenation using hydrogen gas and Raney nickel to yield the corresponding amino compound, in accordance with the procedure recorded by M. Senkus, *J. Am. Chem. Soc.*, 68, 12-14 (1946). After the hydrogenation is completed, the catalyst is removed by filtration and the methanol solvent is removed at reduced pressure yielding N-methyl-N-(2-amino-2-methyl-propyl)-pyrrolidinium bis(trifluoromethylsulfonimide).

Example 10

Here, N-methyl-N-(2-aldimino-2-methyl-propyl)-pyrrolidinium bis(trifluoromethylsulfonimide) is prepared by adding with mixing and in the absence of solvent, 1 equivalent of solid para-formaldehyde to N-methyl-N-(2-amino-2-methylpropyl)-pyrrolidinium bis(trifluoromethylsulfonimide) from Example 9. The mixture is stirred and heated to a temperature of 70° C. for a period of time of 5 hours.

Example 11

To one equivalent of N-methyl-N-(2-aldimino-2-methylpropyl)-pyrrolidinium bis(trifluoromethylsulfonimide) from Example 10 contained in a distillation apparatus with a septum plugged side-arm, under a vacuum of 0.7 mbar, is injected one equivalent of ethyl cyanoacetate. The mixture is heated to a temperature of 150° C., at which point ethyl cyanoacrylate monomer distils and is collected an appropriate receiving flask.

Example 12

3-Isopropenyl-α,α-dimethylbenzylamine was prepared by using a modified procedure from that described by Trumbo et al., *J. Appl. Polym. Sci., Vol.* 82, 1030-1039 (2001).

To 3-isopropenyl-α,α-dimethylbenzylisocyanate (Cytec TMI®, 20 g, 0.1 mol) and dibutyltindilaurate (0.08 g, 0.001 mol) was added dropwise with stirring methanol (3.2 g, 0.1 mol). The reaction mixture was maintained at a temperature below 40° C. After the addition was complete the reaction mixture was heated to a temperature of 60° C. for a period of time of 4 hours. On cooling, the reaction mixture solidified, furnishing 3-isopropenyl-α,α-dimethylbenzyl methyl urethane in almost quantitative yield (23 g, 98%).

The methyl urethane (23 g, 0.01 mol) prepared above was dissolved in butyl cellosolve (25 mls). A solution of KOH (9.3 g, 0.015 mol) in butyl cellosolve (40 mls) was added and the reaction was allowed to progress at reflux temperature for a period of time of 4 hours. After this time the reaction mixture was distilled and 3-isopropenyl-α,α-dimethylbenzylamine was collected at a temperature of 80° C. and 1 mbar vacuum. (Yield: b q, 40%) FTIR: (KBr, cm$^{-1}$) 3357, 3285, 3085, 2965, 2867, 1628, 1599, 1578, 1485, 1458, 1375, 1362, 1294, 1224, 1089, 1009, 890, 800, 724, 697. $^1$H NMR: (CDCl$_3$, 0.3% TMS v/v, ppm) 7.36 (s, 1H), 7.25 (m, 3H), 5.35 (s, 1H), 5.05 (s, 1H), 2.15 (s, 3H) 1.59 2H) 1.4 (s, 6H). GC-MS: M=175, C$_{12}$H$_{17}$N, retention time 5.25 minutes, M/Z=160, M$^+$-CH$_3$.

Example 13

Here, 3-isopropenyl-α,α-dimethylbenzylimine is prepared from the corresponding amine prepared in Example 12 above. 3-isopropenyl-α,α-dimethylbenzylamine (6 g, 0.034 mol) is mixed with an equimolar amount of solid paraformaldehyde (1.05 g, 0.034 mol), and allowed to stir overnight at room temperature and then under modestly elevated temperature conditions for an additional 6 hours. Anhydrous sodium sulphate is added to the mixture and 3-isopropenyl-α,α-dimethylbenzylimine is recovered by vacuum distillation.

What is claimed is:

1. A process for the preparation of a reactive electron deficient olefin, steps of which comprise:
   (a) providing:
      an imine within structure II:

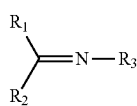

II wherein R$_1$-R$_2$ are each independently selected from the group consisting of H, alkenyl, and alkynyl; and R$_3$ is a hydrocarbon moiety comprising a tertiary carbon which is attached to the N atom, wherein the tertiary carbon atom is attached to or part of one or more substituents selected from the group consisting of linear, branched, and cyclic, or one or more together form a cyclic or polycyclic (as the case may be) structure, which itself(themselves) may have substituents attached thereto; and
      a compound containing a methylene linkage having at least one electron withdrawing substituent attached thereto, wherein the electron withdrawing substituent is selected from the group consisting of nitrile, carboxylic acids, carboxylic esters, sulphonic acids, ketones and nitro;
   (b) reacting the imine of structure II and the compound under appropriate conditions and for a time sufficient to yield a reactive electron deficient olefin; and performing one of 1. step (c), 2. steps (c) and (d), or 3. step (e), as follows
   (c) separating from the reaction mixture of step (b) the so formed reactive electron deficient olefin to yield the reactive electron deficient olefin;
   (d) reacting an amine formed in reaction step (b) and following separation step (c) with formaldehyde or a source thereof to reform the imine of structure II;
   (e) repeating steps (b) through (d), wherein the imine is an ionic liquid having a melting point less than 100° C., which in its molten form contains only ions.

2. The process of claim 1,

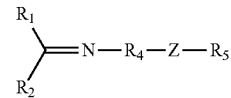

wherein the reactive electron deficient olefin is a 2-cyanoacrylate ester, and the compound containing a methylene linkage having at least one electron withdrawing substituent attached thereto is an alkyl cyanoacetate.

3. A process for the preparation of a vinylidene cyanide, steps of which comprise
   (a) providing as reactants a mixture of formaldehyde or a source thereof and a primary amine having a nitrogen atom attached to a tertiary carbon atom to form an imine;
   (b) providing malononitrile and reacting the imine from step (a) therewith; and
   (c) optionally separating from the mixture the so-formed vinylidene cyanide to yield vinylidene cyanide; and
   (d) optionally either:
      (1) separating from the treatment of step (c) the so formed amine or
      (2) separating from the treatment of step (c) the so formed amine and reacting the amine with formaldehyde or a source thereof to form an imine; and
   (e) optionally repeating steps (b), (c) and (d), wherein the imine is an ionic liquid having a melting point less than 100° C., which in its molten form contains only ions.

4. A process for the preparation of a vinylidene alkylmalonate, steps of which comprise
   (a) providing as reactants a mixture of formaldehyde or a source thereof and a primary amine having a nitrogen atom attached to a tertiary carbon atom to form an imine;
   (b) providing an dialkylmalonate and reacting the imine from step (a) therewith; and
   (c) optionally separating from the mixture the so-formed vinylidene dialkylmalonate ester to yield vinylidene dialkylmalonate ester; and
   (d) optionally either:
      (1) separating from the treatment of step (c) the so formed amine or
      (2) separating from the treatment of step (c) the so formed amine and reacting the amine with formaldehyde or a source thereof to form an imine; and
   (e) optionally repeating steps (b), (c) and (d), wherein the imine is an ionic liquid having a melting point less than 100° C., which in its molten form contains only ions.

5. The process of claim 1, wherein the compound containing a methylene linkage having at least one electron withdrawing substituent attached thereto is an ester of cyanoacetic acid.

6. The process of claim 1, wherein the electron deficient olefin is a compound having one end terminating with a cyanoacrylate, cyanopentadienoate, or alkylene derived from dimalonate and another end terminating with a group selected from the group consisting of branched and unbranched alkyl esters, esters containing aromatics and heterocylic nuclei, acrylates, cyanoacrylates, siloxanes, blocked and unblocked isocyanates, anhydrides, silanes, vinyls, and acetylenes.

7. The process of claim 1, wherein the electron deficient olefin is a 2-cyanoacrylate.

8. The process of claim 7, wherein the 2-cyanoacrylate is selected from the group consisting of methyl, ethyl, n-propyl, i-propyl, propargyl, n-butyl, i-butyl, n-pentyl, n-hexyl, 2-ethylhexyl, n-octyl, n-nonyl, oxononyl, n-decyl, n-dodecyl, allyl, ethynyl, 2-butenyl, cyclohexyl, phenyl, phenethyl, tetrahydrofurfuryl, chloroethyl, 2,2,2-trifluoroethyl, hexafluoroisopropyl, methoxymethyl, methoxyethyl, methoxybutyl, ethoxyethyl, propoxyethyl, butoxymethyl, butoxyethyl and dimethylsiloxane esters of 2-cyanoacrylic acid.

9. The process of claim 1, wherein the imine is not distillable at a pressure of 1 mBar and a temperature of 100° C.

10. The process of claim 3, wherein the imine is not distillable at a pressure of 1 mBar and a temperature of 100° C.

11. The process of claim 4, wherein the imine is not distillable at a pressure of 1 mBar and a temperature of 100° C.

12. The process of claim 3, wherein after performing steps (a) and (b), performing one of 1. step (c), 2. steps (c) and (d), or 3. step (e), as follows
 (c) separating from the reaction mixture of step (b) the so formed reactive electron deficient olefin to yield the reactive electron deficient olefin;
 (d) reacting an amine formed in reaction step (b) and following separation step (c) with formaldehyde or a source thereof to reform the imine of structure II;
 (e) repeating steps (b) through (d).

13. The process of claim 4, wherein after performing steps (a) and (b), performing one of 1. step (c), 2. steps (c) and (d), or 3. step (e), as follows
 (c) separating from the reaction mixture of step (b) the so formed reactive electron deficient olefin to yield the reactive electron deficient olefin;
 (d) reacting an amine formed in reaction step (b) and following separation step (c) with formaldehyde or a source thereof to reform the imine of structure II;
 (e) repeating steps (b) through (d).

* * * * *